United States Patent
Inaba et al.

(10) Patent No.: US 9,872,914 B2
(45) Date of Patent: Jan. 23, 2018

(54) SOLID PHARMACEUTICAL COMPOSITION CONTAINING 1-(3-(2-(1-BENZOTHIOPHEN-5-YL)ETHOXY)PROPYL)AZETIDIN-3-OL OR SALT THEREOF

(71) Applicant: TOYAMA CHEMICAL CO., LTD., Shinjuku-ku (JP)

(72) Inventors: Hiroyuki Inaba, Toyama (JP); Mitsuhiro Nagata, Toyama (JP)

(73) Assignee: TOYAMA CHEMICAL CO., LTD., Shinjuku-ku (JP)

( * ) Notice: Subject to any disclaimer, the term of this patent is extended or adjusted under 35 U.S.C. 154(b) by 0 days.

(21) Appl. No.: 14/379,960

(22) PCT Filed: Feb. 21, 2013

(86) PCT No.: PCT/JP2013/054268
§ 371 (c)(1),
(2) Date: Aug. 20, 2014

(87) PCT Pub. No.: WO2013/125617
PCT Pub. Date: Aug. 29, 2013

(65) Prior Publication Data
US 2015/0045345 A1    Feb. 12, 2015

(30) Foreign Application Priority Data
Feb. 22, 2012  (JP) ................... 2012-035710

(51) Int. Cl.
| | | |
|---|---|---|
| C07D 205/00 | (2006.01) | |
| C07D 333/00 | (2006.01) | |
| C07D 333/56 | (2006.01) | |
| A61K 31/397 | (2006.01) | |
| A61K 31/38 | (2006.01) | |
| A61K 47/36 | (2006.01) | |
| C07D 409/12 | (2006.01) | |
| A61K 9/20 | (2006.01) | |
| A61K 9/28 | (2006.01) | |
| A61K 47/10 | (2017.01) | |

(52) U.S. Cl.
CPC ............ *A61K 47/36* (2013.01); *A61K 9/2018* (2013.01); *A61K 9/2027* (2013.01); *A61K 9/2054* (2013.01); *A61K 9/2095* (2013.01); *A61K 9/282* (2013.01); *A61K 9/2866* (2013.01); *A61K 31/397* (2013.01); *A61K 47/10* (2013.01); *C07D 409/12* (2013.01); *A61K 9/2059* (2013.01); *A61K 9/288* (2013.01)

(58) Field of Classification Search
USPC ......... 548/952; 549/49, 58; 514/210.01, 443
See application file for complete search history.

(56) References Cited

U.S. PATENT DOCUMENTS

| | | | | |
|---|---|---|---|---|
| 2004/0253690 | A1* | 12/2004 | Kubota | ............... C12P 19/12 435/100 |
| 2005/0070521 | A1 | 3/2005 | Saitoh et al. | |
| 2006/0205709 | A1 | 9/2006 | Kimura et al. | |
| 2007/0196494 | A1* | 8/2007 | Grenier | ............... A61K 9/0056 424/487 |
| 2009/0069576 | A1 | 3/2009 | Saitoh et al. | |
| 2009/0087485 | A1* | 4/2009 | Pilgaonkar et al. | ........... 424/464 |
| 2009/0209512 | A1* | 8/2009 | Iwakami | ............... A61K 31/397 514/210.19 |
| 2010/0075941 | A1 | 3/2010 | Kimura et al. | |
| 2011/0046115 | A1* | 2/2011 | Ahmed et al. | ........... 514/214.02 |

FOREIGN PATENT DOCUMENTS

| | | |
|---|---|---|
| EP | 2048145 A1 | 4/2009 |
| JP | 2007-137802 | 6/2007 |
| WO | 03/035647 | 5/2003 |
| WO | WO 03051338 A1 * | 6/2003 ........... A61K 9/0056 |
| WO | 2004/091605 | 10/2004 |
| WO | WO 2006058250 A2 * | 6/2006 ........... A61K 9/0056 |
| WO | 2006/104088 | 10/2006 |
| WO | WO 2009084017 A2 * | 7/2009 |

OTHER PUBLICATIONS

Buhler, V. et al., Pharmaceutical Technology of BASF Excipients. Published 2008.*
Humbert et al., (J. Alzheimers Disease vol. 19, pp. 1185-1197 published 2010).*
Kimura et al (British Journal of Pharmacology vol. 157, pp. 451-463, 2009).*
Kimura et al (British Journal of Pharmacology vol. 157, pp. 451-463, 2009),.*
Buhler et al (Pharmaceutical Technology of BASF excipients, published 2008).*
Ward et al (J. Pharmaceutical Sciences vol. 58, pp. 1464-1467, Published 1969).*
Kimura (British Journal of Pharmacology vol. 157, pp. 451-463, 2009).*
International Search Report dated Mar. 26, 2013 in PCT/JP13/054268 filed Feb. 21, 2013.
Fukumuro, K., "Device for Increasing Compliance 2", Clinician, vol. 91, No. 405, pp. 1019-1022, 1991.
Kitamori, N., "Hardness of Tablets", Pharm Tech Japan, vol. 19, No. 12, pp. 61(2069)-67(2075), 2003.

(Continued)

*Primary Examiner* — Timothy Thomas
*Assistant Examiner* — George W Kosturko
(74) *Attorney, Agent, or Firm* — Oblon, McClelland, Maier & Neustadt, L.L.P.

(57) ABSTRACT

This solid pharmaceutical composition is useful as a solid pharmaceutical composition of 1-(3-(2-(1-benzothiophen-5-yl)ethoxy)propyl)azetidin-3-ol, which is excellently elutable and moldable and is stable in long-term storage, or a salt thereof.

16 Claims, No Drawings

(56) References Cited

OTHER PUBLICATIONS

Ichibagase, H. et al., "Development of Pharmaceutical Product", $1^{st}$ Edition, Hirokawa Shoten Co., vol. 12, pp. 178-185, 1990.
Chinese Official Action dated May 4, 2016, in Chinese Patent Application No. 201380010472.9, with Japanese translation, (11 pages).

\* cited by examiner

SOLID PHARMACEUTICAL COMPOSITION CONTAINING 1-(3-(2-(1-BENZOTHIOPHEN-5-YL)ETHOXY) PROPYL)AZETIDIN-3-OL OR SALT THEREOF

TECHNICAL FIELD

The present invention relates to a solid pharmaceutical composition comprising 1-(3-(2-(1-benzothiophen-5-yl) ethoxy)propyl)azetidin-3-ol or a salt thereof and one or more selected from mannitol, sorbitol and isomaltose.

BACKGROUND ART 1-(3-(2-(1-Benzothiophen-5-yl)ethoxy)propyl)azetidin-3-ol (hereinafter referred to as "Compound A") or a salt thereof is a compound having neuroprotective, nerve regeneration-promoting and neurite outgrowth effects, and useful as a therapeutic agent for central and peripheral neurological diseases (Patent Document 1).

Compound A or a salt thereof is orally administered. Thus, there is a need for an oral formulation comprising Compound A or a salt thereof. The most preferred dosage form in general is a tablet (Non-Patent Document 1). However, Compound A or a salt thereof has properties such as low compression moldability, proneness to a tableting trouble (sticking), and insufficient preservation stability at high humidity.

In producing tablets, a mixed powder for tableting is required to have compression moldability. Low compression moldability of the mixed powder for tableting decreases the hardness of tablets. In this case, there is a fear of damage of tablets in packaging or transportation or abrasion or chipping of tablets in a coating machine in film-coating of the tablets.

The method, which involves blending a highly moldable excipient such as crystalline cellulose to produce a mixed powder for tableting having a high compression moldability to produce tablets having necessary hardness (Non-Patent Document 2), has been reported (Non-Patent Document 3).

The tablet or the like, which contains Compound A or a salt thereof, lactose, crystalline cellulose and a diluent, is known (Patent Document 2), however, there is a need for improvements in dissolvability and stability under preservation conditions of heating and moisturizing.

PRIOR ART DOCUMENTS

Patent Document

Patent Document 1: Pamphlet of International Publication No. WO 2003/035647
Patent Document 2: Pamphlet of International Publication No. WO 2004/091605

Non-Patent Document

Non-Patent Document 1: Kenji Fukumuro, "Konpuraiansu wo ageru kufuh 2 (Device for Increasing Compliance 2)", CLINICIAN, '91, No. 405, p. 1020, 1991
Non-Patent Document 2: Pharm Tech Japan, 19 (12), p. 61 (2069)-p. 67 (2075)
Non-Patent Document 3: Hisashi Ichibagase, et al. (Eds.), "Iyakuhin No Kaihatsu (Development of Pharmaceutical Product)", vol. 12, 1st Edition, Hirokawa Shoten Co., vol. 12, Oct. 15, 1990, p. 178-185

SUMMARY OF INVENTION

Technical Problem

There is a need for a solid pharmaceutical composition comprising Compound A or a salt thereof, excellent in dissolvability and moldability, and further stable during long-term preservation.

Solution to Problem

As a result of intensive studies under such circumstances, the present inventors have found a solid pharmaceutical composition comprising Compound A or a salt thereof, excellent in dissolvability and moldability, and further stable during long-term preservation, thereby accomplishing the present invention.

Advantageous Effects of the Invention

The solid pharmaceutical composition comprising Compound A or a salt thereof and one or more selected from mannitol, sorbitol and isomaltose according to the present invention is excellent in dissolvability and moldability, and further stable during long-term preservation.

The solid pharmaceutical composition of the present invention is useful as a solid pharmaceutical composition of Compound A or a salt thereof.

DESCRIPTION OF EMBODIMENTS

The present invention will be described below in detail.

As used herein, % means percentage by mass unless otherwise noted.

The solid pharmaceutical composition of the present invention comprises Compound A or a salt thereof and one or more selected from mannitol, sorbitol and isomaltose.

Compound A or a salt thereof used in the present invention can be produced by a method as described, for example, in International Publication No. WO 03/035647.

The content rate of Compound A or a salt thereof contained in the solid pharmaceutical composition of the present invention is 0.1 to 96%, preferably 30 to 90%, more preferably 40 to 90%, or still more preferably 45 to 87%.

Examples of the salt of Compound A can include commonly known salts at basic groups such as an amino group.

Salts at basic groups include, for example, salts with mineral acids such as hydrochloric acid, hydrobromic acid, nitric acid and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid and trifluoroacetic acid; and salts with sulfonic acids such as methanesulfonic acid, benzenesulfonic acid, p-toluenesulfonic acid, mesitylenesulfonic acid and naphthalenesulfonic acid.

Among the above salts, preferred salts include pharmacologically acceptable salts, and the maleate is more preferable.

Compound A or a salt thereof of the present invention encompasses solvates, hydrates and crystals in various forms thereof.

The solid pharmaceutical composition of the present invention comprises one or more selected from mannitol, sorbitol and isomaltose, and preferably comprises mannitol.

Mannitol used in the present invention is not particularly limited; however, examples thereof include Parteck M 200 (Merck & Co., Inc.).

The total content rate of one or more selected from mannitol, sorbitol and isomaltose contained in the solid pharmaceutical composition is 1 to 98%, preferably 6 to 60%, or more preferably 6 to 51%.

Preferably, the solid pharmaceutical composition of the present invention further comprises a disintegrant.

Examples of the disintegrant used in the present invention include cellulose derivatives such as carmellose, carmellose calcium, croscarmellose sodium and low-substituted hydroxypropylcellulose; starch derivatives such as sodium carboxymethyl starch and partially pregelatinized starch; and polypyrrolidone derivatives such as crospovidone; preferred are cellulose derivatives, more preferably carmellose, carmellose calcium and croscarmellose sodium, or still more preferably croscarmellose sodium.

Croscarmellose sodium is not particularly limited; however, examples thereof include Primellose (DMV-Fonterra Excipients GmbH & Co., KG), Ac-Di-Sol (FMC) and Kiccolate (Nichirin Chemical Industries, Ltd.).

The content rate of the disintegrant contained in the solid pharmaceutical composition is 0 to 10%, or preferably 0 to 5%.

Preferably, the solid pharmaceutical composition of the present invention further comprises a lubricant.

Examples of the lubricant used in the present invention include sodium stearyl fumarate, stearic acid, magnesium stearate, calcium stearate, talc and sucrose fatty acid ester; preferred are magnesium stearate and sodium stearyl fumarate, more preferably magnesium stearate.

The content rate of the lubricant contained in the solid pharmaceutical composition is 0.5 to 3%, or preferably 1 to 2%.

The solid pharmaceutical composition of the present invention can further comprise a diluent.

Examples of the diluent include sugar alcohols such as erythritol and xylitol; saccharides such as saccharose, powder sugar, lactose and glucose; cyclodextrins such as α-cyclodextrin, β-cyclodextrin, γ-cyclodextrin, hydroxypropyl β-cyclodextrin and sodium sulfobutylether β-cyclodextrin; celluloses such as crystalline cellulose and microcrystalline cellulose; starches such as corn starch, potato starch and a partially pregelatinized starch; phosphates such as calcium hydrogen phosphate and anhydrous dibasic calcium phosphate; and carbonates such as precipitated calcium carbonate. These diluents may be added singly or in combinations of two or more.

The amount to be added of the diluent contained in the solid pharmaceutical composition is not particularly limited, and the amount thereof depending on the dosage form may be added.

The form of the solid pharmaceutical composition of the present invention is preferably a tablet, or more preferably a film-coated tablet.

The solid pharmaceutical composition of the present invention can use additives commonly used in pharmacological agents in the range not impairing the advantages of the present invention.

Examples of such additives include a binder, a corrigent, a coloring agent, a flavoring agent, a surfactant, a fluidizing agent, a coating agent and a plasticizer.

Examples of the binder include hydroxypropyl cellulose, carmellose sodium, polyvinyl pyrrolidone, polyvinyl alcohol, hypromellose and methylcellulose.

Examples of the corrigent include aspartame, saccharin, stevia, thaumatin and acesulfame potassium.

Examples of the coloring agent include titanium dioxide, iron sesquioxide, yellow iron sesquioxide, black iron oxide, edible red 102, edible yellow 4 and edible yellow 5.

Examples of the flavoring agent include essential oils such as orange oil, lemon oil, mentha oil and pine oil; essences such as orange essence and peppermint essence; flavors such as cherry flavor, vanilla flavor and fruit flavor; powdered flavors such as apple micron, banana micron, peach micron, strawberry micron and orange micron; vanillin; and ethylvanillin.

Examples of the surfactant include sodium lauryl sulfate, dioctyl sodium sulfosuccinate, polysorbates, sorbitan fatty acid esters and polyoxyethylene hydrogenated castor oils.

Examples of the fluidizing agent include silica dioxides such as light anhydrous silicic acid and hydrated silicon dioxide.

Examples of the coating agent include hypromellose, aminoalkylmethacrylate copolymer E, aminoalkylmethacrylate copolymer RS, ethyl cellulose, cellulose acetate phthalate, hypromellose phthalate, hypromellose acetate succinate, methacrylic acid copolymer L, methacrylic acid copolymer LD and methacrylic acid copolymer S.

Examples of the plasticizer include triethyl citrate, macrogol, triacetin and propylene glycol.

These additives may be used singly or in combinations of two or more. The amount thereof blended is not particularly limited, and the additives may be properly blended so that the effect thereof is sufficiently exerted depending on the particular purpose for which the additive is intended.

The method, dose and frequency of administration of the solid pharmaceutical composition of the present invention can be properly selected depending on the age, body weight and symptoms of a patient; however, the composition may be administered once or in several divided portions in a daily dose capable of exerting the drug effect thereof, and may be typically administered to an adult once or in several divided portions in a daily dose of, for example, 40 to 1,000 mg in terms of Compound A.

Methods for producing the solid pharmaceutical composition of the present invention include a method involving tableting a granulated product obtained by a wet granulation method or a dry granulation method, or a direct tableting method.

Examples of the wet granulation method include fluidized-bed granulation, wet crushing granulation, extrusion granulation and stirring granulation.

Examples of the dry granulation method include a compacting method, a slagging method and a briquetting method.

Preferred methods for producing the solid pharmaceutical composition of the present invention include a direct tableting method and a dry granulation method.

Preferred dry granulation methods include a compacting method and a slagging method; more preferred is a compacting method. Examples of the compacting method include a method involving producing a compression molded product using a roller compactor and crushing the product to provide granulated particles. The roller compression pressure in the roller compactor varies depending on the machine type used; however, it is preferably 3 to 9 Mpa when TF-LABO or TF-MINI (both are manufactured by Freund Corporation) is used.

The method for producing the solid pharmaceutical composition of the present invention by a dry granulation method is preferably a method which involves (1) adding a portion of a lubricant to Compound A or a salt thereof and mixing the resultant, (2) performing granulation by a dry granulation method, (3) causing the resultant granulated powder to pass through a sieve, (4) adding the residual lubricant, a disintegrant, a diluent and an excipient, and mixing the resultant, and (5) tableting the mixture.

The usefulness of the solid pharmaceutical composition of the present invention will now be described with reference to the following Test Examples.

Test Example 1

Uncoated tablets and film-coated tablets in Example 1 and Comparative Example 1 were used as samples.

The hardness of the uncoated tablets was measured three times using a tablet hardness tester (Tablet Hardness Tester 8M, manufactured by Schleuniger).

The dissolution test of the film-coated tablets was performed by the dissolution test specified in the Japanese Pharmacopoeia (paddle method). The number of revolutions of the paddle was set at 50 rpm. Each sample was charged into 900 mL of USP dissolution test solution (pH 6.8), and the resultant test solution after 15 minutes was collected to determine the dissolution rate (%) of Compound A by an optical density method. The pH 6.8 dissolution test solution was prepared by dissolving 272.2 g of potassium dihydrogen phosphate in water, adding 179.2 mL of 5 mol/L sodium hydroxide thereto, adjusting the solution to 2,000 mL with water, taking 300 mL thereof, and mixing the resultant in 5,700 mL of water.

The film-coated tablet using lactose and crystalline cellulose as diluents (Comparative Example 1) had a dissolution rate of less than 85% after 15 minutes, whereas the tablet using mannitol as a diluent (Example 1) had a dissolution rate of 85% or more after 15 minutes, showing a highly excellent dissolvability.

The uncoated tablet of Example 1 also had necessary hardness.

The uncoated tablet in which Compound A or a salt thereof and mannitol were blended had hardness comparable to that of the uncoated tablet in which lactose and crystalline cellulose were blended, and the film-coated tablet of Example 1 was excellent as a tablet having more sufficient dissolvability.

Test Example 2

Uncoated tablets and film-coated tablets in Examples 3 to 6 and Comparative Examples 2 to 4 were used as samples.

The measurement of the hardness of the uncoated tablets and the dissolution test of the film-coated tablets were performed in the same way as in Test Example 1.

The results are shown in Table 2.

TABLE 2

|  | Example 3 | Example 4 | Example 5 | Example 6 | Comparative Example 2 | Comparative Example 3 | Comparative Example 4 |
|---|---|---|---|---|---|---|---|
| Maleate of Compound A [mg] | 111.88 | 111.88 | 111.88 | 111.88 | 111.88 | 111.88 | 111.88 |
| Mannitol [mg] | 126.87 | 126.87 | 0.0 | 0.0 | 0.0 | 0.0 | 0.0 |
| Isomaltose [mg] | 0.0 | 0.0 | 126.87 | 0.0 | 0.0 | 0.0 | 0.0 |
| Sorbitol [mg] | 0.0 | 0.0 | 0.0 | 126.87 | 0.0 | 0.0 | 0.0 |
| Erythritol [mg] | 0.0 | 0.0 | 0.0 | 0.0 | 126.87 | 0.0 | 0.0 |
| Xylitol [mg] | 0.0 | 0.0 | 0.0 | 0.0 | 0.0 | 126.87 | 0.0 |
| Sucrose [mg] | 0.0 | 0.0 | 0.0 | 0.0 | 0.0 | 0.0 | 95.15 |
| Crystalline Cellulose [mg] | 0.0 | 0.0 | 0.0 | 0.0 | 0.0 | 0.0 | 31.72 |
| Croscarmellose Sodium [mg] | 7.5 | 7.5 | 7.5 | 7.5 | 7.5 | 7.5 | 7.5 |
| Magnesium Stearate [mg] | 3.75 | 0.0 | 3.75 | 3.75 | 3.75 | 3.75 | 3.75 |
| Sodium Stearyl Fumarate [mg] | 0.0 | 3.75 | 0.0 | 0.0 | 0.0 | 0.0 | 0.0 |
| Mass of Uncoated Tablet [mg] | 250.0 | 250.0 | 250.0 | 250.0 | 250.0 | 250.0 | 250.0 |
| Hardness of Uncoated Tablet [N] | 111 | 120 | 111 | 123 | 28 | 42 | 55 |
| Dissolution Rate of Film-Coated Tablet [%] | 99.8 | 98.4 | 89.1 | 87.9 | 97.7 | 97.6 | 85.8 |

The results are shown in Table 1.

TABLE 1

|  | Example 1 | Comparative Example 1 |
|---|---|---|
| Maleate of Compound A [mg] | 111.88 | 111.86 |
| Mannitol [mg] | 121.87 | 0.0 |
| Lactose [mg] | 0.0 | 92.82 |
| Crystalline Cellulose [mg] | 0.0 | 30.94 |
| Croscarmellose Sodium [mg] | 12.50 | 12.50 |
| Magnesium Stearate [mg] | 3.75 | 1.875 |
| Mass of Uncoated Tablet [mg] | 250.0 | 250.0 |
| Hardness of Uncoated Tablet [N] | 92 | 91 |
| Dissolution Rate of Film-Coated Tablet [%] | 96.8 | 82.8 |

The uncoated tablets using mannitol, isomaltose or sorbitol as a diluent (Examples 3 to 6) had necessary hardness, and the corresponding film-coated tablets had excellent dissolution rates of 85% or more after 15 minutes. Also for the formulations in which sodium stearyl fumarate was used as a lubricant in the tablet using mannitol as a diluent (Example 4), the uncoated tablet had necessary hardness, and the film-coated tablet was excellent in dissolvability.

In contrast, the hardness of the uncoated tablet using erythritol, xylitol as well as sucrose and crystalline cellulose as a diluent (Comparative Examples 2 to 4) was extremely low.

The film-coated tablets, wherein Compound A or a salt thereof and mannitol, sorbitol or isomaltose were blended, had excellent dissolvability, and the corresponding uncoated tablets were excellent as uncoated tablets having necessary hardness.

Test Example 3

Film-coated tablets in Examples 3 and 7 to 13 were used as samples.

The total amount of related substances contained in each film-coated tablet and the amount of a particular related substance (D1 form) were measured at the beginning of test and after storage for 4 weeks and 3 months under conditions of 40° C. and a relative humidity of 75%. The D1 form is 3-((3-(2-(1-benzothiophen-5-yl)ethoxy)propyl)amino)propan-1,2-diol.

The related substances were measured under the following conditions.

Measurement Condition
Detector: ultraviolet absorptiometer
Measurement wavelength: 230 nm
Column: Xterra RP18 (manufactured by Waters), 5 µm, 4.6×150 mm
Precolumn: Xterra RP18 (manufactured by Waters), 5 µm, 3.9×20 mm
Column temperature: constant temperature around 40° C.
Mobile phase A: 0.2 mol/L phosphate buffer (pH 3.0):water: acetonitrile=10:85:5 (volume ratio)
Mobile phase B: 0.2 mol/L phosphate buffer (pH 3.0):water: acetonitrile=10:40:50 (volume ratio)

The 0.2 mol/L phosphate buffer was prepared by the following method.

To 12.25 g of potassium dihydrogen phosphate, water was added to provide a total amount of 450 mL. To this solution, a phosphoric acid solution, wherein 13.7 mL of phosphoric acid (a guaranteed reagent, manufactured by Wako Pure Chemical Industries, Ltd.) was diluted to 1,000 mL by adding water, was added to adjust to pH 3.0.

Feed of mobile phase: the concentration gradient was controlled by varying the mixing ratio between the mobile phases A and B as follows.

| Time from Post-Injection (minutes) | Mobile Phase A (vol %) | Mobile Phase B (vol %) |
| --- | --- | --- |
| 0~30 | 100→0 | 0→100 |
| 30~40 | 0 | 100 |
| 40~50 | 0→100 | 100→0 |
| 50~55 | 100 | 0 |

Flow rate: 1.0 mL/minute

The results are shown in Table 3. In the table, N. D. means below the limit of detection.

TABLE 3

|  |  | Example 3 | Example 7 | Example 8 | Example 9 | Example 10 | Example 11 | Example 12 | Example 13 |
| --- | --- | --- | --- | --- | --- | --- | --- | --- | --- |
| Maleate of Compound A [mg] |  | 111.88 | 111.88 | 111.88 | 111.88 | 111.88 | 111.88 | 111.88 | 111.88 |
| Mannitol [mg] |  | 126.87 | 126.87 | 126.87 | 126.87 | 126.87 | 126.87 | 126.87 | 134.37 |
| Croscarmellose Sodium [mg] |  | 7.5 | 0.0 | 0.0 | 0.0 | 0.0 | 0.0 | 0.0 | 0.0 |
| Carmellose [mg] |  | 0.0 | 7.5 | 0.0 | 0.0 | 0.0 | 0.0 | 0.0 | 0.0 |
| Carmellose Calcium [mg] |  | 0.0 | 0.0 | 7.5 | 0.0 | 0.0 | 0.0 | 0.0 | 0.0 |
| Low-Substituted Hydroxypropylcellulose [mg] |  | 0.0 | 0.0 | 0.0 | 7.5 | 0.0 | 0.0 | 0.0 | 0.0 |
| Sodium Carboxymethyl Starch [mg] |  | 0.0 | 0.0 | 0.0 | 0.0 | 7.5 | 0.0 | 0.0 | 0.0 |
| Crospovidone [mg] |  | 0.0 | 0.0 | 0.0 | 0.0 | 0.0 | 7.5 | 0.0 | 0.0 |
| Partially Pregelatinized Starch [mg] |  | 0.0 | 0.0 | 0.0 | 0.0 | 0.0 | 0.0 | 7.5 | 0.0 |
| Magnesium Stearate [mg] |  | 3.75 | 3.75 | 3.75 | 3.75 | 3.75 | 3.75 | 3.75 | 3.75 |
| Mass of Uncoated Tablet [mg] |  | 250.0 | 250.0 | 250.0 | 250.0 | 250.0 | 250.0 | 250.0 | 250.0 |
| Total Amount of Related Substances [%] | At Beginning | 0.163 | 0.146 | 0.117 | 0.141 | 0.144 | 0.136 | 0.146 | 0.148 |
|  | After 4 Weeks | 0.176 | 0.166 | 0.173 | 0.310 | 0.540 | 0.442 | 0.312 | 0.306 |
|  | After 3 Months | 0.302 | 0.179 | 0.295 | 0.693 | 1.603 | 1.057 | 0.685 | 0.655 |
| Amount of Related Substance D1 [%] | At Beginning | N.D. | N.D. | N.D. | N.D. | N.D. | ND. | N.D. | N.D. |
|  | After 4 Weeks | 0.017 | 0.010 | 0.018 | 0.036 | 0.067 | 0.062 | 0.035 | 0.035 |
|  | After 3 Months | 0.089 | 0.043 | 0.083 | 0.188 | 0.431 | 0.300 | 0.181 | 0.184 |

In the film-coated tablet using croscarmellose sodium, carmellose or carmellose calcium as a disintegrant (Example 3, 7 or 8), no significant increase in related substances was observed after storage for 4 weeks under conditions of 40° C. and a relative humidity of 75%. In addition, in the film-coated tablets of Examples 3, 7 and 8, no significant increase in the related substances was observed even after storage for 3 months under conditions of 40° C. and a relative humidity of 75%.

In contrast, an about 2- to 3-fold increase in the total amount of the related substances and an about 2- to 7-fold increase in the particular related substance (D1 form) were observed after storage for 4 weeks under conditions of 40° C. and a relative humidity of 75% in the film-coated tablet using low-substituted hydroxypropylcellulose, sodium carboxymethyl starch, crospovidone or partially pregelatinized starch as a disintegrant (Examples 9 to 12) and the film-coated tablet not using any disintegrant (Example 13) compared to in the film-coated tablets of Examples 3, 7 and 8. In addition, an about 2- to 8-fold increase in the total amount of the related substances and an about 2- to 10-fold increase in the particular related substance were observed after storage for 3 months under conditions of 40° C. and a relative humidity of 75% in the film-coated tablets of Examples 9 to 12 and 13 compared to in the film-coated tablets of Examples 3, 7 and 8.

The film-coated tablet using croscarmellose sodium, carmellose or carmellose calcium as a disintegrant (Example 3, 7 or 8) had extremely excellent stability.

Among others, the tablet, wherein Compound A or a salt thereof, mannitol and croscarmellose sodium, carmellose or carmellose calcium were blended, had excellent dissolvability, and was excellent as a tablet stable during long-term preservation.

Test Example 4

Uncoated tablets and film-coated tablets in Examples 14 and 15 were used as samples.

The measurement of the hardness of uncoated tablets and the dissolution test of film-coated tablets were performed in the same way as in Test Example 1.

The results are shown in Table 4.

TABLE 4

|  | Example 14 | Example 15 |
|---|---|---|
| Maleate of Compound A [mg] | 187.50 | 223.76 |
| Mannitol [mg] | 51.25 | 14.99 |
| Croscarmellose Sodium [mg] | 7.50 | 7.50 |
| Magnesium Stearate [mg] | 3.75 | 3.75 |
| Mass of Uncoated Tablet [mg] | 250.0 | 250.0 |
| Content Rate of Maleate of Compound A [%] | 75.0 | 89.5 |
| Hardness of Uncoated Tablet [N] | 90 | 69 |
| Dissolution Rate of Film-Coated Tablet [%] | 90.9 | 85.2 |

The film-coated tablets highly containing Compound A or a salt thereof (Examples 14 and 15) had dissolution rates of 85% or more after 15 minutes, showing highly excellent dissolvability.

The uncoated tablets of Examples 14 and 15 also had necessary hardness.

The present invention will now be described with reference to Examples and Comparative Examples. However, the present invention is not intended to be limited thereby.

The maleate of Compound A, which was sieved with a sieve having an opening of 500 µm, was used.

Unless otherwise limited, mannitol (Parteck M 200, manufactured by Merck & Co., Inc.) and croscarmellose sodium (Primellose, manufactured by DMV-Fonterra Excipients GmbH & Co., KG) used were ones each sieved with a sieve having an opening of 850 µm, and magnesium stearate (Magnesium Stearate, manufactured by Merck & Co., Inc.) used was one sieved with an opening of 180 µm.

As a coating agent was used Opadry 03F44057 (hypromellose 2910: 71.5%, macrogol 6000: 14.166%, talc: 7.167%, titanium oxide: 7.067%, iron sesquioxide: 0.1%, manufactured by Nippon Colorcon).

As carnauba wax was used Polishing Wax-105 (manufactured by Nippon Wax).

TF-LABO (roll pressurization: 3 Mpa, manufactured by Freund Corporation) was used as a dry granulating machine; HTP 18A (manufactured by Hata Iron Works Co., Ltd.), as a tableting machine; and DRC-200 (manufactured by Powrex Corporation), as a film-coating machine.

The formulations produced in the following Examples and Comparative Examples were each a round tablet having a diameter of about 8.5 mm and a thickness of about 4.1 to 4.7 mm.

Example 1

To 4.48 g of the maleate of Compound A, 4.87 g of mannitol and 0.50 g of croscarmellose sodium were added, and the resultant was manually mixed for 5 minutes. To this mixed powder, 0.1491 g of magnesium stearate was added, and the resultant was manually mixed for 5 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 2

To 452.82 g of the maleate of Compound A, 2.5296 g of magnesium stearate was added, and the resultant was mixed for 30 minutes. This mixed powder was compression-molded using a dry granulating machine, and the molded solid product was sized. To 100.00 g of the obtained sized powder, 112.77 g of mannitol and 6.67 g of croscarmellose sodium were added, and the resultant was mixed for 10 minutes. To this mixed powder, 2.7776 g of magnesium stearate was added, and the resultant was mixed for 30 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 3

To 53.70 g of the maleate of Compound A, 60.90 g of mannitol and 3.60 g of croscarmellose sodium were added, and the resultant was mixed for 10 minutes. To this mixed powder, 1.80 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 4

To 4.48 g of the maleate of Compound A, 5.07 g of mannitol and 0.30 g of croscarmellose sodium were added, and the resultant was manually mixed for 5 minutes. To this mixed powder, 0.1499 g of sodium stearyl fumarate (PRUV, manufactured by JRS Pharma GmbH & Co. KG) was sieved with a sieve having an opening of 180 µm and added, and the resultant was manually mixed for 5 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 5

To 4.48 g of the maleate of Compound A, 5.07 g of isomaltose (galenIQ 720, manufactured by Higuchi Inc.) and 0.30 g of croscarmellose sodium were sieved with a sieve having an opening of 850 μm and added, respectively, and the resultant was manually mixed for 5 minutes. To this mixed powder, 0.1505 g of magnesium stearate was added, and the resultant was manually mixed for 5 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 6

To 4.48 g of the maleate of Compound A, 5.07 g of sorbitol (Parteck SI 150, manufactured by Merck & Co., Inc.) and 0.30 g of croscarmellose sodium were sieved with a sieve having an opening of 850 μm and added, respectively, and the resultant was manually mixed for 5 minutes. To this mixed powder, 0.1503 g of magnesium stearate was added, and the resultant was manually mixed for 5 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 7

To 53.70 g of the maleate of Compound A, 60.90 g of mannitol and 3.60 g of carmellose (NS-300, manufactured by Gotoku Chemical Company Ltd.) were sieved with a sieve having an opening of 850 μm and added, respectively, and the resultant was mixed for 10 minutes. To this mixed powder, 1.80 g of magnesium stearate was added, the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 8

To 53.70 g of the maleate of Compound A, 60.90 g of mannitol and 3.60 g of carmellose calcium (E.C.G-505, manufactured by Gotoku Chemical Company Ltd.) were sieved with a sieve having an opening of 850 μm and added, respectively, and the resultant was mixed for 10 minutes. To this mixed powder, 1.80 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 9

To 53.70 g of the maleate of Compound A, 60.90 g of mannitol and 3.60 g of low-substituted hydroxypropylcellulose (L-HPC LH-11, manufactured by Shin-Etsu Chemical Co., Ltd.) were sieved with a sieve having an opening of 850 μm and added, respectively, and the resultant was mixed for 10 minutes. To this mixed powder, 1.80 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 10

To 53.70 g of the maleate of Compound A, 60.90 g of mannitol and 3.60 g of sodium carboxymethyl starch (Primojel, manufactured by DMV-Fonterra Excipients GmbH & Co., KG) were sieved with a sieve having an opening of 850 μm and added, respectively, and the resultant was mixed for 10 minutes. To this mixed powder, 1.80 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 11

To 53.70 g of the maleate of Compound A, 60.90 g of mannitol and 3.60 g of crospovidone (Polyplasdone XL-10, manufactured by ISP) were sieved with a sieve having an opening of 850 μm and added respectively, and the resultant was mixed for 10 minutes. To this mixed powder, 1.80 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 12

To 53.70 g of the maleate of Compound A, 60.90 g of mannitol and 3.60 g of partially pregelatinized starch (Starch 1500, manufactured by Nippon Colorcon) were sieved with a sieve having an opening of 850 µm and added, respectively, and the resultant was mixed for 10 minutes. To this mixed powder, 1.80 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 13

To 53.70 g of the maleate of Compound A, 64.50 g of mannitol was added, and the resultant was mixed for 10 minutes. To this mixed powder, 1.80 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 14

To 398.45 g of the maleate of Compound A, 1.57 g of magnesium stearate was added, and the resultant was mixed for 30 minutes. This mixed powder was compression-molded using a dry granulating machine, and the molded solid product was sized. To 120.00 g of the obtained sized powder, 32.69 g of mannitol and 4.78 g of croscarmellose sodium were added, and the resultant was mixed for 10 minutes. To this mixed powder, 1.99 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Example 15

To 398.45 g of the maleate of Compound A, 1.57 g of magnesium stearate was added, and the resultant was mixed for 30 minutes. This mixed powder was compression-molded using a dry granulating machine, and the molded solid product was sized. To 120.00 g of the obtained sized powder, 8.02 g of mannitol and 4.01 g of croscarmellose sodium were added, and the resultant was mixed for 10 minutes. To this mixed powder, 1.67 g of magnesium stearate was added, and the resultant was mixed for 30 minutes. This obtained mixed powder was subjected to tableting at a tableting pressure of about 10 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Comparative Example 1

To 174.03 g of the maleate of Compound A, 0.9726 g of magnesium stearate was added, and the resultant was mixed for 30 minutes. This mixed powder was compression-molded using a dry granulating machine, and the molded solid product was sized. To 60.0 g of the obtained sized powder, 49.51 g of lactose (FlowLac 90, manufactured by Meggle Japan Co., Ltd.), 16.50 g of crystalline cellulose (Ceolus PH 302, manufactured by Asahi Kasei Chemicals Corporation) and 6.67 g of croscarmellose sodium were sieved with a sieve having an opening of 850 µm and added, respectively, and the resultant was mixed for 10 minutes. To this mixed powder, 0.6667 g of magnesium stearate was added, and the resultant was mixed for 30 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Comparative Example 2

To 4.48 g of the maleate of Compound A, 5.07 g of erythritol (Erythritol, manufactured by B Food Science Co., Ltd.) and 0.30 g of croscarmellose sodium were sieved with a sieve having an opening of 850 µm and added, respectively, and the resultant was manually mixed for 5 minutes. To this mixed powder, 0.1497 g of magnesium stearate was added, and the resultant was manually mixed for 5 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Comparative Example 3

To 4.48 g of the maleate of Compound A, 5.07 g of xylitol (Xilite, manufactured by Towa Chemical Industry Co., Ltd.) and 0.30 g of croscarmellose sodium were sieved with a sieve having an opening of 850 µm and added, respectively, and the resultant was manually mixed for 5 minutes. To this mixed powder, 0.1490 g of magnesium stearate was added, and the resultant was manually mixed for 5 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

Comparative Example 4

To 4.48 g of the maleate of Compound A, 3.81 g of sucrose (Frost Sugar, Nissin Sugar Co., Ltd.), 1.27 g of crystalline cellulose (Ceolus PH 302, manufactured by Asahi Kasei Chemicals Corporation) and 0.30 g of croscarmellose sodium were sieved with a sieve having an opening of 850 µm and added, respectively, and the resultant was manually mixed for 5 minutes. To this mixed powder, 0.1497 g of magnesium stearate was added, and the resultant was manually mixed for 5 minutes. This obtained mixed powder was subjected to tableting at a tableting pressure of about 12 kN using a pestle having a double rounded surface with a tablet diameter of 8.5 mm to obtain round uncoated tablets of 250 mg per tablet. The uncoated tablets were coated with 8 mg of a coating agent per tablet, followed by adding a minute amount of carnauba wax thereto to obtain film-coated tablets.

INDUSTRIAL APPLICABILITY

The solid pharmaceutical composition comprising Compound A or a salt thereof and one or more selected from mannitol, sorbitol and isomaltose according to the present invention is excellent in dissolvability and moldability and stable during long-term preservation.

The solid pharmaceutical composition of the present invention is useful as a solid pharmaceutical composition of Compound A or a salt thereof.

The invention claimed is:

1. A solid pharmaceutical tablet composition, comprising:
   44% to 89% of 1-(3-(2-(1-benzothiophen-5-yl)ethoxy) propyl)azetidin-3-ol or a salt thereof;
   6% to 51% of at least one selected from the group consisting of mannitol, sorbitol, and isomaltose;
   3% to 5% of a disintegrant selected from the group consisting of carmellose, carmellose calcium, croscarmellose sodium, low-substituted hydroxypropylcellulose, sodium carboxymethyl starch, partially pregelatinized starch, crospovidone, and a combination thereof; and
   1% to 2% of a lubricant selected from the group consisting of magnesium stearate, sodium stearyl fumarate, and a combination thereof.

2. The solid pharmaceutical tablet composition of claim 1, which comprises mannitol.

3. The solid pharmaceutical tablet composition of claim 1, wherein the 1-(3-(2-(1-benzothiophen-5-yl)ethoxy)propyl) azetidin-3-ol or the salt thereof is present in an amount of from 45% to 87% of a total weight of the solid pharmaceutical tablet composition.

4. The solid pharmaceutical tablet composition of claim 1, wherein the disintegrant is at least one selected from the group consisting of carmellose, carmellose calcium, croscarmellose sodium, and low-substituted hydroxypropylcellulose.

5. The solid pharmaceutical tablet composition of claim 1, wherein the disintegrant is at least one selected from the group consisting of carmellose, carmellose calcium, and croscarmellose sodium.

6. The solid pharmaceutical tablet composition of claim 1, wherein the lubricant is present in an amount of 1.5% of a total weight of the solid pharmaceutical tablet composition.

7. The solid pharmaceutical tablet composition of claim 1, wherein the lubricant is magnesium stearate.

8. The solid pharmaceutical tablet composition of claim 1, wherein the tablet is a film-coated tablet.

9. The solid pharmaceutical tablet composition of claim 1, which comprises sorbitol.

10. The solid pharmaceutical tablet composition of claim 1, which comprises isomaltose.

11. The solid pharmaceutical tablet composition of claim 1, wherein the solid pharmaceutical tablet composition has a hardness of from 69 to 123N.

12. The solid pharmaceutical tablet composition of claim 1, wherein the solid pharmaceutical tablet composition has a dissolution rate of 85% or more after 15 minutes, and the dissolution rate is measured by a paddle method comprising setting a number of paddle revolution at 50 rpm, adding a sample of the solid pharmaceutical tablet composition to 900 mL of a test solution having a pH value of 6.8 and comprising water, potassium dihydrogen phosphate, and sodium hydroxide, leaving the test solution to which the sample is added for 15 minutes, and determining the dissolution rate of the 1-(3-(2-(1-benzothiophen-5-yl)ethoxy)propyl)azetidin-3-ol or the salt thereof by an optical density method.

13. The solid pharmaceutical tablet composition of claim 1, wherein the solid pharmaceutical tablet composition has a hardness of from 69 to 123N and a dissolution rate of 85% or more after 15 minutes, and the dissolution rate is measured by a paddle method comprising setting a number of paddle revolution at 50 rpm, adding a sample of the solid pharmaceutical tablet composition to 900 mL of a test solution having a pH value of 6.8 and comprising water, potassium dihydrogen phosphate, and sodium hydroxide, leaving the test solution to which the sample is added for 15 minutes, and determining the dissolution rate of the 1-(3-(2-(1-benzothiophen-5-yl)ethoxy)propyl)azetidin-3-ol or the salt thereof by an optical density method.

14. The solid pharmaceutical tablet composition of claim 1, wherein the disintegrant comprises croscarmellose sodium.

15. The solid pharmaceutical tablet composition of claim 2, wherein the disintegrant is croscarmellose sodium, and the lubricant is magnesium stearate.

16. The solid pharmaceutical tablet composition of claim 2, wherein the 1-(3-(2-(1-benzothiophen-5-yl)ethoxy)propyl)azetidin-3-ol or the salt thereof is present in an amount of from 44% to 75% of a total weight of the solid pharmaceutical tablet composition, the mannitol is present in an amount of from 6% to 49% of the total weight of the solid pharmaceutical tablet composition, the disintegrant is croscarmellose sodium, and the lubricant is magnesium stearate.

* * * * *